United States Patent [19]

Mitchiner

[11] 4,275,734
[45] Jun. 30, 1981

[54] CRYOSURGICAL APPARATUS AND METHOD

[75] Inventor: Robert K. Mitchiner, Longmont, Colo.

[73] Assignee: Valleylab, Inc., Boulder, Colo.

[21] Appl. No.: 824,174

[22] Filed: Aug. 12, 1977

[51] Int. Cl.³ ............................................. A61B 17/36
[52] U.S. Cl. .............................. 128/303.1; 62/514 JT
[58] Field of Search .................... 128/303.1, DIG. 27; 62/514 JT

[56] References Cited

U.S. PATENT DOCUMENTS

| Re. 28,657 | 12/1975 | Barger et al. | 128/303.1 |
|---|---|---|---|
| 3,536,075 | 10/1970 | Thomas, Jr. | 128/303.1 |
| 3,696,813 | 10/1972 | Wallach | 128/303.1 |
| 3,913,581 | 10/1975 | Ritson et al. | 128/303.1 |
| 3,924,628 | 12/1975 | Droegemueller et al. | 128/303.1 |
| 3,971,383 | 7/1976 | Van Gerven | 128/303.1 |
| 3,993,075 | 11/1976 | Lisenbee et al. | 128/303.1 |
| 4,018,227 | 4/1977 | Wallach | 128/303.1 |

FOREIGN PATENT DOCUMENTS 1455251 9/1966 France .

OTHER PUBLICATIONS

*Anesthesiology* vol. 38, No. 3; pp. 280-283; Mar. 1973.

Primary Examiner—Dalton L. Truluck
Assistant Examiner—C. F. Rosenbaum
Attorney, Agent, or Firm—Gerald J. Ferguson, Jr.; Joseph J. Baker

[57] ABSTRACT

Cryosurgical apparatus for necrosing human tissue or the like, the apparatus comprising a coolant supply where coolant comprising nitrous oxide, carbon dioxide, Freon 13 or Freon 23 is disposed within a container as a liquid under its own vapor pressure; pressure elevating means for increasing the vapor pressure so that it is greater than what it would be at room temperature and for maintaining the elevated vapor pressure substantially constant; a cryosurgical instrument having a hollow tissue contacting portion and a coolant expansion means disposed at the distal end of a feed passageway and a discharge path disposed outside of the passageway; and means for supplying the coolant to the feed passageway of the cryosurgical instrument so that the temperature of the coolant discharged through the expansion means is lowered. Means are also disclosed including switchable valve means connected to the discharge path of the cryosurgical instrument, the switchable valve means being switchable to a first position freeze mode to exhaust the coolant from the apparatus and to a second position defrost mode for closing the switchable valve means; defrost discharge means also connected to the discharge path of the cryosurgical instrument, the flow impedance of the defrost discharge means being substantially greater than that of the switchable valve means when it is in its first position freeze mode and substantially less than that of the switchable valve means when it is in its second position defrost mode.

56 Claims, 3 Drawing Figures

- - - FREEZE GAS FLOW PATH
— · — DEFROST GAS FLOW PATH

CRYOSURGICAL APPARATUS AND METHOD

BACKGROUND OF THE INVENTION

1. Field of the Invention

This invention relates to an improved cryosurgical apparatus and method and, in particular to apparatus and a method for improving the freezing and defrosting procedures utilized in cryosurgery.

2. Discussion of the Prior Art

Cryosurgery by definition is the use of extreme cold to perform various surgical procedures, most of which require the killing of living tissue. One early use of cooling by gas expansion described by Amoils was the removal of cataracts by freezing a small diameter probe to the cataract and then pulling to remove the cataract from the eye. Later Dr. I. S. Cooper used cryosurgery to destroy brain tissue as a treatment for Parkinson's disease. Then in the 1960's a device was designed to treat various gynecological disorders. This was a hand held unit which was equipped with interchangeable tips and operated by pressing a "trigger" in the handle which initiated coolant flow to cool the tip in contact with the tissue to be treated. These systems normally use carbon dioxide ($CO_2$) or nitrous oxide ($N_2O$) for coolants because they are readily available and may be stored for indefinite periods.

The physical phenomena which produce the cooling are, in order of importance, evaporation and the Joule-Thompson Effect. Since the boiling points of nitrous oxide and carbon dioxide are $-88°$ C. and $-78°$ C. respectively at atmospheric pressure, they produce temperatures approaching these levels when they are expanded into a cryosurgical tip or probe through an orifice or expansion tube. The Joule-Thompson effect is the cooling generated when a high pressure gas is expanded through an orifice to a lower pressure. The Joule-Thompson coefficient relates change of temperature to change in pressure.

$$U = dT/dP$$

where

U is the Joule-Thompson coefficient
dT is the change in temperature
dP is the change in pressure.

The Joule-Thompson coefficient for nitrous oxide, for example, is 0.7165. If this is substituted into the equation to determine dT using full cylinder pressure of 50 atmospheres (750 psi) exhausted to the atmosphere, the resulting dT is:

$$dT = U\, dP$$
$$dT = .7165\,(-50)$$
$$= 35.83 C \text{ maximum } dT$$

When this is applied at body temperature, which is nominally $37°$ C., the body temperature is reduced to $1°$ C. which is not low enough to generate tissue destruction. Tissue necrosis is generally accepted to occur at approximately $-21.2°$ C., the tissue eutectic temperature. Therefore, the basic contribution of the Joule-Thompson effect is to initially cool the tube which is feeding more gas to the expansion site, thus producing two-phase flow, i.e., liquid and gas, in the expansion tube. This mixture is sprayed onto the inner surfaces of the tip, evaporates, cools the tip, and is then exhausted. In route to the exhaust port the cold gas from the tip passes around the metal tube which is feeding the coolant to the tip. The incoming coolant in the metal tube is then super-cooled and liquefies, ultimately supplying 100% liquid to the tip. This is called regeneration and occurs in most cyosurgical instruments where feedline and exhaust are coaxial.

Thus, the Joule-Thompson effect produces enough cooling to initiate the freezing portion of a cryosurgical procedure and evaporation does the rest. This is also indicated by the fact that in well designed probes, tip temperatures often approach the boiling points of the coolants, i.e. about $-80°$ C. See "Anesthesiology", Vol. 38, No. 3, March 1973, pp. 280-282 for an additional discussion of the Joule-Thompson effect.

When the freezing portion of the procedure is completed, it is necessary to thaw the frozen area to remove the probe. To accomplish this conventionally the flow of the coolant is shut off downstream of the tip. With the gas flow stopped, the entire system is brought to pressure equilibrium ($\simeq 750$ psi) and since the tip is very cold, the gaseous coolant in the immediate area is liquified, thus warming the tip to just above the freezing point of water. A variation of this method is to completely reverse the flow of the coolant generating the same effect, i.e., transient exothermic liquid generation. Defrost temperatures generated by these means tend to be transient. That is, in the exhaust shut off method of defrost the temperature will usually rise to approximately $2°$ C. and then begin to fall back below freezing. This becomes a significant problem if the gas supply pressure is higher than the nominal (750 psi at $68°$ F.) in accordance with this invention as will be described in more detail hereinafter. As pressure increases defrost becomes increasingly ineffective, ultimately preventing ice ball release and removal from the operative site.

The mechanism of tissue destruction in cryosurgery is generally accepted to be rupture of the cell membrane resulting in cell death. It is well known that a cell can accommodate reduced temperatures by dehydrating into the intracellular interticies where freezing does no damage to the cell. This dehydration can be accomplished successfully by the cell only if the freezing rate is slow enough to permit adequate dehydration; higher freezing rates produces intercellular ice which expands on freezing and ruptures the cell membrane. Slow rates approximately $178°$ C. per minute are used to preserve biologic samples i.e. bovine sperm, etc. Faster rates generated by conventional cryosurgery systems are in the order of $5°$ C./sec ($300°$ C./min) and usually cause unpredictable necrosis. This leads to the limited acceptance of cryosurgery as a viable means of treatment. This poor predictability then becomes a most significant problem of conventional cryosurgery.

This is worsened by the fact that as a conventional cryosurgical procedure progresses the pressure in the supply cylinder will decay. This is caused by evaporative cooling of the metal cylinder and its liquid contents as the liquid evaporates to supply coolant to the probe. Thus, the duration of the procedure is limited by gas pressure decay as is the possibility of doing repetitive procedures one after another since gas supplies must be changed or there must be a wait until the pressure recovers. Although the problem of decreasing gas pressure can be somewhat lessened by employing larger supply coolant cylinders, these are different to procure, fill and store, compared to the "E" sized cylinders which are universally available for all procedures.

Another shortcoming associated with the prior art is as follows. Conventionally depth of necrosis is judged by the thickness of ice generated around the tip during the procedure. Since ice generation requires only 0° C. and the removal of the latent heat, this is a poor method because it does not adequately predict the depth of necrosis.

SUMMARY OF THE INVENTION

It is thus a primary object of this invention to provide an improved method and apparatus for implementing cryosurgical treatment in a predictable and effective manner.

It is a further object of this invention to provide a method and apparatus of the above type where the desired depth of necrosis can be substantially established before the procedure commences.

It is a further object of this invention to provide a method and apparatus of the above type where defrosting can be implemented in an effective manner with rapid release from the treated area, if necessary.

It is a further object of this invention to provide a method and apparatus of the above type which may be used with "E" sized coolant supply cylinders or the like without being limited by gas pressure decay and which may be employed in repetitive procedures which are performed one after another.

It is a further object of this invention to provide a method and apparatus of the above type which reduces the time required for procedures, reduces patient discomfort and ensures repeatable results.

These and other objects of the invention will become apparent from the reading of the following specification and claims taken together with the drawing.

DETAILED DESCRIPTION OF THE PREFERRED EMBODIMENT OF THE INVENTION

Figure 1:
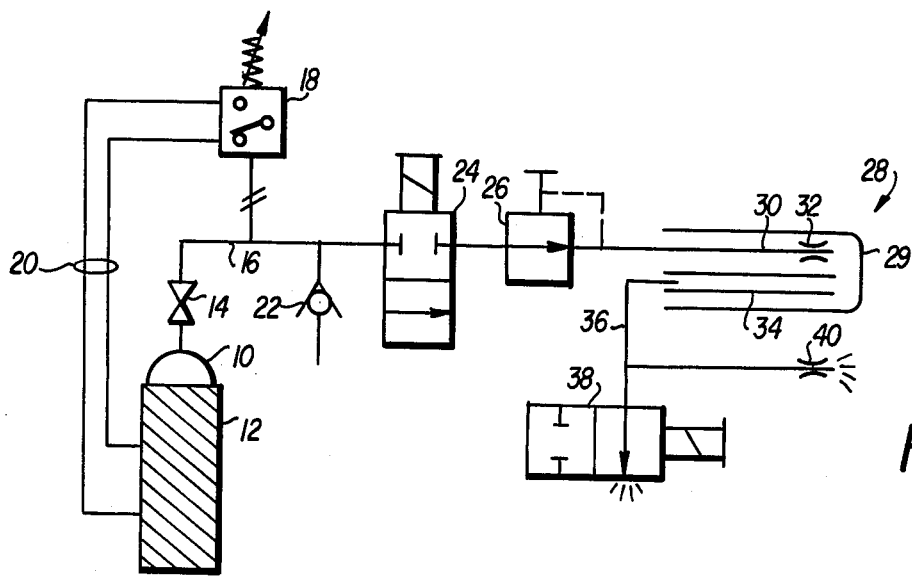
FIG. 1 is a schematic diagram of a first illustrative embodiment of the invention where a common pressure is employed for both the freeze and defrost modes of operation.

Referring to the drawing where like reference numerals refer to like parts and in particular, in FIG. 1, there is illustrated a schematic diagram of a first embodiment of the invention where a common pressure is employed for both the freeze and defrost modes of operation, as will be described in more detail hereinafter. A coolant supply or supply cylinder 10, such as an "E" sized cylinder containing the coolant, is heated by a heat source 12 which may be a mantle disposed about the cylinder in accordance with the invention. The mantle contains electrical resistance wire (not shown) through which current may flow to heat the cylinder. The coolant may be a polyatomic gas such as nitrous oxide, carbon dioxide, Freon 13 and Freon 23, the latter two gases being supplied by DuPont. The coolant is stored in the cylinder as a liquid at room temperature under its own vapor pressure. By heating the cylinder, the pressure of the gas within the cylinder may be elevated.

The supply 10 is connected via an isolation valve 14 to line or duct 16. Connected to line 16 is a pressure sensing means or pressure switch 18 which transduces the pressure sensed in line 16 to an electrical signal which is applied over lines 20 to control heat source 12 and thereby maintain the pressure in supply 10 at a predetermined level in accordance with an aspect of this invention. For example, if the coolant is nitrous oxide, the pressure at which the nitrous oxide might be maintained would be approximately 900 psi. This is done by raising and maintaining the temperature of cylinder 10 at approximately 83° F. In particular, the operation of switch 18 might be such that whenever the pressure dropped to 890 psi, it would turn heat source 12 on until the pressure reached 910 psi, at which time, source 12 would be cut off until the pressure again dropped to 890 psi. Hence, the vapor pressure in the cylinder is elevated to and maintained at a level, in accordance with this invention, which is substantially higher than its room temperature level—that is, approximately 750 psi at 68° F., for example. A relief valve 22 may be connected to line 16 whereby if the pressure within the line rises above 1,000 psi, for example, the valve opens to prevent the buildup of such excessive pressures.

Line 16 may also be connected to a two-way valve 24 which is normally closed. When the valve is in the closed position shown in FIG. 1, coolant will not flow through line 16. However, when it is raised, the coolant will flow to an adjustable pressure regulator 26, which may be a conventional diaphram type regulator. Assuming nitrous oxide at approximately 900 psi is maintained in supply 10, the operation of regulator 26 may be such that the output pressure therefrom may be adjusted from 600 to 850 psi, for example. The output coolant from regulator 26 is then applied to a cryosurgical instrument which is generally indicated at 28. As indicated hereinbefore, a typical cryosurgical instrument includes a hollow tissue contacting portion generally indicated at 29 through which extends an inner tube or coolant feed passageway which is schematically indicated at 30. The inner tube 30 has an orifice or expansion tube at the distal end thereof, the orifice being schematically indicated at 32. A discharge path for the coolant is typically concentrically disposed about the inner tube 30. However, for purposes of illustration, the discharge path is indicated at 34 and is shown in a side-by-side relationship within the tube 30. Since the instrument itself forms no part of this invention, and since such instruments are well known in this art (see U.S. Pat. Nos. 3,696,813; 3,913,581; U.S. Pat. No. Re. 28,657 and U.S. Pat. No. 3,924,628, for example, which are hereby incorporated herein by reference), the foregoing schematic illustration of the probe 28 has been employed. It should be noted that the tissue contacting portion of the instrument may be a tubular tip such as shown at 2A in above U.S. Pat. No. 3,913,581 or an inflatable bladder such as shown at 11 in U.S. Pat. No. 3,924,628.

The coolant in discharge path 34 is then exhausted through line or duct 36. Line 36 is connected to a normally open two-way valve or switchable valve means 38. When the valve is in a first position, the position shown in FIG. 1, the coolant in line 36 will be exhausted to the atmosphere, for example, through the valve. Thus, in the freeze mode of operation, the valve 38 is in the position shown in FIG. 1. In the defrost mode of operation, valve 38 is moved to the right, its second position, whereby the valve is closed and the coolant in line 36 is exhausted out of a defrost discharge means where the flow impedance of defrost discharge means 40 is substantially greater than that of valve 38 when it is open and substantially less than that of the valve when it is closed. Defrost discharge means 40 may be an orifice or an adjustable flow valve. Thus, the mode of operation is switched from freeze to defrost simply by switching valve 38, assuming valves 14 and 24 are open.

Figure 2:
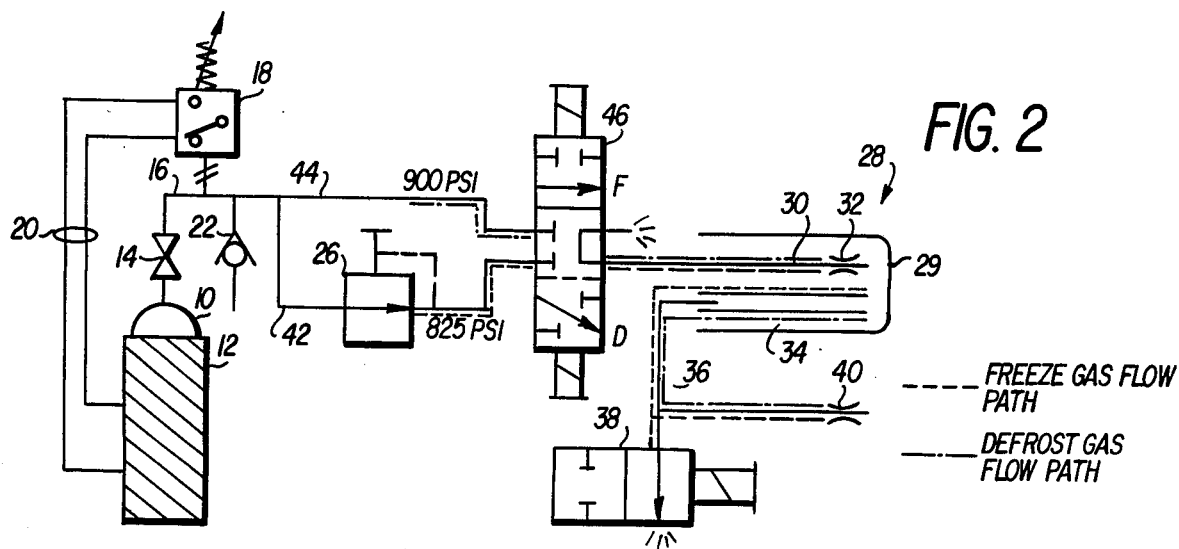
FIG. 2 is a schematic diagram of a second illustrative embodiment of the invention where the pressure for controlling the freeze rate during the freeze mode is variable, while the pressure employed during the defrost mode is fixed.

Reference should now be made to FIG. 2. In this embodiment the pressure for controlling the freeze rate is variable while the pressure employed for defrosting is fixed, as will be explained in more detail hereinafter. Line 16 is branched into first and second paths or lines 42 and 44. The pressure in line 44 corresponds to that in the supply 10. However, the coolant in line 42 is applied to adjustable pressure regulator 26, such that the output pressure thereof is adjustable depending upon the setting of the regulator. As indicated hereinbefore, if nitrous oxide is employed and the pressure in supply 10 is maintained at approximately 900 psi, the output pressure of the coolant from regulator 26 may be adjusted from 600 to 850 psi while the pressure in line 44 would be maintained at approximately 900 psi. The output from regulator 26 and line 44 are connected to a mode selector valve or further switchable valve 46 which may either be a four-way tandem center valve or a three-way valve with no center position, for example. When the valve is depressed such that the section thereof labeled F is in position, the system is placed in its freeze mode of operation. Thus, the output from regulator 26 is connected to probe 28 to appropriately lower the temperature of the tissue contacting portion. Freeze valve 38 will be in its normally open position shown in FIG. 2, whereby the coolant will exhaust therethrough as described hereinbefore. The neutral center position is as shown in FIG. 2 and is employed as a cutoff position and to vent coolant from the instrument as indicated in the FIG. Preferably the coolant should be vented prior to each freeze cycle.

When mode valve 46 is elevated so that the D portion thereof is in position, line 44 is connected to probe 28 whereby coolant at 900 psi, for example, is supplied to the probe. At this time, valve 38 is closed and thus, the coolant in line 36 is exhausted out defrost orifice 40 in the manner described hereinbefore. The freeze and defrost gas flow paths are as indicated in FIG. 2.

It should also be understood that two separate coolant supplies may be respectively used for the freeze and defrost modes of operation where each coolant supply may have the output pressure therefrom regulated by its own pressure regulator 26 as in FIG. 1. The outputs of the regulators may then be applied to a mode selector switch corresponding to switch 46 where the output of the switch would be connected to probe 28 as in FIG. 2.

As stated hereinbefore, the mechanism of tissue destruction in cryosurgery is generally accepted to be rupture of the cell membrane resulting in cell death. It is well known that a cell can accommodate reduced temperatures by dehydrating into the intracellular interticies where freezing does no damage to the cell. This dehydration can be accomplished successfully by the cell only if the freezing rate is slow enough to permit adequate dehydration; higher freezing rates produce intercellular ice which expands on freezing and ruptures the cell membrane. Faster rates generated by conventional cryosurgery systems are in the order of 5° C./sec and usually cause unpredictable necrosis. In accordance with the present invention, it has been found that freezing rates of at least 15° C./sec and preferably 20° C./sec are necessary to cause effective necrosis. Rates of this order cause rapid growth of intercellular ice and the subsequent rupture of the cell membrane.

It has been found that the role the temperature of tissue contacting portion 29 plays in generating necrosis is limited to the temperature differential produced to force high rate freezing to occur deeper in the tissue. For example a rate of 20° C./sec reaching an ultimate temperature of −40° C. may effectively necrose 2 mm. deep while 20° C./sec to −60° C. may necrose 3 mm. deep. Vascularity in the area to be treated by cryosurgery has been said to reduce the effectiveness of the procedure. It is believed that when freezing rates in the order of at least 15° C./sec are applied, the vascularity effect disappears, or at least becomes insignificant.

Figure 3:
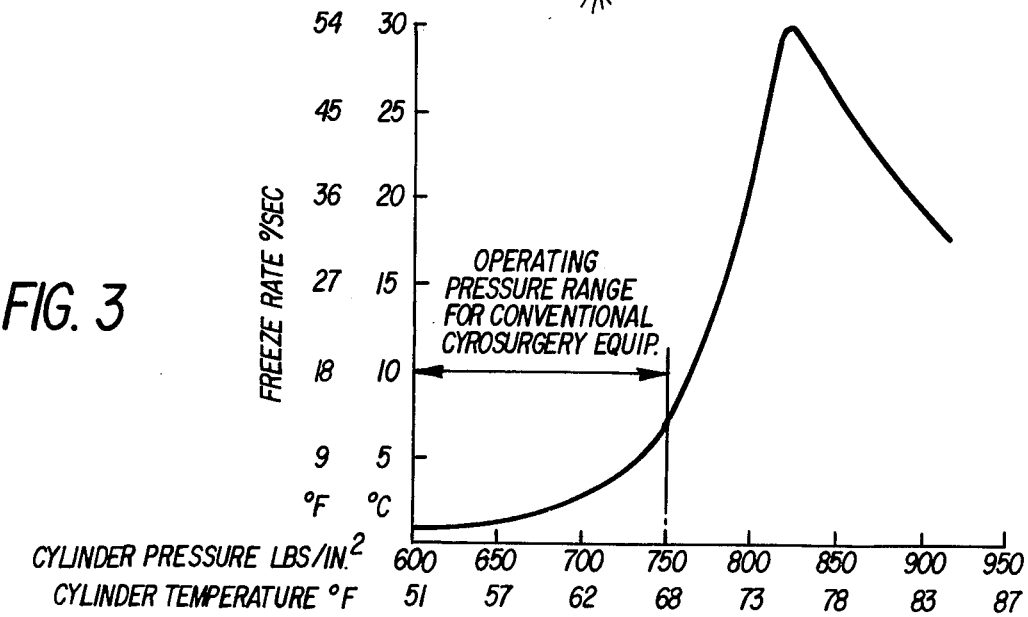
FIG. 3 is a graph illustrating the variation of freeze rate with respect to coolant supply pressure obtainable with this invention.

Referring to FIG. 3, conventional cryosurgery systems operate in the range shown on the curve and since no control is exerted over supply pressure, freeze rate control is impossible. This causes necrotic effect to be unpredictable and leads to the limited acceptance of cryosurgery as a viable means of treatment. This poor predictability then becomes a most significant problem of conventional cryosurgery.

This is worsened by the fact that as the procedure progresses the pressure in the supply cylinder will decay. This is caused by evaporative cooling of the metal cylinder and its liquid contents as the liquid evaporates to supply coolant to the probe. Also depth of necrosis is conventionally judged by the thickness of ice generated around the tip during the procedure. Since ice generation requires only 0° C. and the removal of the latent heat, this is a poor method since it does not adequately predict the depth of necrosis.

Thus, in accordance with the invention, a method and apparatus is provided to guarantee fully controlled freezing rates by raising and maintaining the coolant pressure substantially constant, as described hereinbefore with respect to FIG. 1. That is, supply cylinder 10 is heated to raise and maintain the cylinder temperature at about 83° F. for $N_2O$, for example, which is equivalent to a vapor pressure of about 900 psi. This 900 psi nitrous oxide is then regulated by regulator 26 to the desired pressure for use as coolant in the instrument and in the FIG. 2 embodiment the 900 psi coolant is used as is for probe warming.

System mode in the FIG. 2 embodiment is selected by positioning valve 46 to supply either freezing or warming gas to the instrument. For the freeze mode, the exhaust is directed through the large orifice of valve 38 which may be in parallel with the defrost discharge means 40. In the warming cycle, the freeze valve is closed so all flow must pass the defrost discharge means 40. Thus for effective cooling, the gas is exhausted through a low flow impedance and warming is accomplished by increasing the exhaust impedance—not a complete blockage.

Warming (defrost) of the tissue contacting portion 29 is produced by continuous liquid generation in the area of portion 29. This is accomplished by controlling the amount of coolant which vents from discharged means 40. Venting must be carefully controlled because too much exhaust will cause a transition back to cooling and not enough flow reduces the warming effect. If the exhaust is reduced too severely or stopped completely, liquid generation becomes a transient phenomena as discussed hereinbefore with respect to the prior art and the effectiveness of the warming is significantly reduced. The position of the defrost gas input should be such that warming gas impinges on the active area of portion 29 for fastest warming.

The system is capable of being operated in two modes of warming. In the FIG. 1 embodiment, the warming cycle is operated at the same pressure as the freeze. This will produce defrosted tip temperatures varying from 10° C. depending on the freeze pressure chosen. It should be appreciated that these temperatures are sufficiently high not only to permit release of the instrument from the treated area but also to effect warming thereof if needed in a particular procedure. Also, it should be noted that the defrost temperature will be maintained as long as the apparatus is in its defrost mode as opposed to the transient nature of the time prior art instruments tend to maintain the defrost temperature. Thus, it is not critical to make sure the instrument is released from the treated area while the defrost temperature is present since this temperature is always present during the defrost mode.

The foregoing advantages are also present in the FIG. 2 embodiment. This embodiment is also particularly helpful when rapid ice ball melting is necessary to reduce the procedure time or for any other reason. To produce this effect the freeze pressure is adjusted independently of the defrost which remains at a preselected pressure which will produce the final tip temperature required, as discussed hereinbefore. It should also be noted that the present invention allows independent control of warming coolant flow. This is unlike the prior art, reverse flow defrost method where defrost flow is controlled by the freeze orifice or expansion needle. The freeze orifice or expansion needle of the present invention is chosen to provide optimum freeze—not optimum defrost.

Because rate of freezing is critically important and since it is a direct function of gas pressure, it should be further appreciated that the use of a regulator alone such as regulator 26 to control pressure to a value lower than normal temperature cylinder pressure will be self defeating except for very shallow necrosis.

In an illustrative but non-limitative embodiment of the invention, which may correspond to FIG. 1 or FIG. 2, the following specific devices and values were employed, the results of testing thereof being illustrated in FIG. 3. Pressure switch 18 was a bourdon tube type dual control pressure switch which applied an electrical current of typically about 10 amperes to line 20 when the pressure in supply cylinder 10 fell about 10 psi below the desired pressure. This output current was maintained until the pressure rose to about 10 psi above the desired pressure, at which time it was cut off until the pressure again fell to the lower limit. The pressure switch is available from the Barksdale Controls Division, Los Angeles, Calif. The wires 20 were directly connected to the heating wire disposed inside the heating mantle 12 where the mantle 12 was covered with fiberglass and operated from a 115 volt AC source, 750 watts for a "G" cylinder and 500 watts for an "E" cylinder. The heating mantle is available from the Briscoe Manufacturing Company, Columbus, Ohio. The supply cylinder 10 was a "G" size cylinder in the tested system. The pressure regulator 26 was of the self-venting, diaphram type. Such a regulator is available from the Tescom Corporation, Minneapolis, Minn. The probe 29 had a 5 mm. diameter and a length of 8 mm. The expansion tube 32 was 8 inches long and had an outside diameter of 0.020 inches and an inside diameter of 0.016 inches, the orifice 32 being 0.016 inches. The output orifice from freeze valve 38 was about 0.093 inches and the defrost orifice 40 comprised a tube 2½ inches long having an outside diameter of 0.016 inches and an inside diameter of 0.008 inches, the orifice 40 being 0.008 inches.

The variations of freeze rate with respect to cylinder pressure (or temperature) is illustrated in FIG. 3 for a system having the parameters specified above where nitrous oxide was employed as the coolant. As can be seen, when the cylinder pressure is less than or equal to room temperature (approximately 68° F.), the freeze rate is no more than about 8° C./second. This, as indicated hereinbefore, is insufficient to provide consistently effective necrosis. By elevating the cylinder pressure in accordance with this invention, the freeze rate can be increased to values substantially in excess of 15° C./second. Thus, as can be seen in FIG. 3, the freeze rate in the specific illustrative embodiment specified above can be increased to about 30° C./second if the cylinder pressure is maintained at about 825 psi. With variations in the above system parameters, the maximum freeze rate obtainable might vary—that is, the maximum freeze rate might be about 25° C./second at 850 psi. In any event, by elevating the cylinder pressure in accordance with this invention, freeze rates in excess of 15° C./second can be readily obtained. As can be seen in the FIG. 3 embodiment, freeze rates in excess of 15° C. are obtained over a substantial range of cylinder pressures commencing with a pressure of about 780 psi and extending to pressures well in excess of 900 psi.

Thus, the apparatus and method of the present invention coupled with the knowledge which relates effectiveness of necrosis with rate of temperature change during the freezing cycle, makes cryosurgical performance predictable. Rate of tip temperature change has been found to be a function of supply pressure, thus it is possible to predict the amount of cell morbidity and depth of necrosis. It is further possible to program the desired depth of necrosis into the apparatus and estimate the effectiveness by monitoring the rate of freeze and ultimate temperature produced during the procedure.

Also some of the features of the constant pressure coolant supply of the present invention improve the useability of cryosurgical systems. One of these features is that the duration of procedures need not be limited by gas pressure decay. It is also possible with a constant pressure coolant supply to do repetitive procedures one after the other without changing gas supplies or waiting for the pressure to recover. It is also possible to use "E" sized cylinders which are universally available for all procedures. This eliminates the difficulty of procuring and filling larger cylinders and reduces the amount of storage area required.

Further, warming (defrost) becomes an active part of the procedure and may improve the efficacy in some cases. It assures effective and rapid release from the treated area. The freeze rate vs. effective necrosis effect makes it possible to significantly reduce the time required for procedures, reduces patient discomfort and ensures repeatable results. This effect also eliminates the need for estimating the depth of necrosis by the prior art method of judging ice ball growth around the periphery of the tip in contact with the tissue.

In summary, the present invention makes predictable, effective cryosurgical treatment possible and makes it possible to actively control tip temperature during defrost.

What is claimed is:

1. Cryosurgical apparatus comprising a coolant supply where a coolant selected from the groups consisting of nitrous oxide, carbon dioxide, Freon 13 or Freon 23 is disposed within a container as a liquid due to the pressure of its own vapor where the critical temperature of said coolant is greater than room temperature;

pressure maintaining means for maintaining said pressure of the vapor at approximately at least what it is at room temperature;

a cryosurgical instrument having a coolant expansion means disposed at the distal end of a feed passageway; and means for supplying said coolant to the feed passageway of said cryosurgical instrument so that the temperature of the coolant discharged through said expansion means is lowered;

whereby said pressure maintaining means maintains said vapor pressure at approximately at least what it is at room temperature during said supplying of the coolant to the feed passageway of the cryosurgical instrument.

2. Apparatus as in claim 1 including switchable valve means connected to said discharge path of said cryosurgical instrument, said switchable valve means being switchable to a first position to exhaust said coolant from said apparatus and to a second position for closing the switchable valve means;

defrost discharge means also connected to said discharge path of said cryosurgical instrument, the flow impedance of said defrost discharge means being substantially greater than that of said switchable valve means when it is in its said first position and substantially less than that of the switchable valve means when it is in its said second position whereby the coolant is supplied to said feed passageway of said cryosurgical instrument for both a freeze mode and a defrost mode of operation of said apparatus, said apparatus being in its freeze mode when said switchable valve means is in its first position so that said coolant discharges through said switchable valve means and said apparatus being in its defrost mode when it is in its second position so that said coolant discharges through said defrost discharge means and where the temperature of said tissue contacting portion in the defrost mode is greater than 0° C. as long as said apparatus is in the latter mode.

3. Apparatus as in claim 2 including an adjustable pressure regulator responsive to the output gas from said coolant supply for adjustably regulating the pressure of the coolant applied to said feed passageway of the cryosurgical instrument.

4. Apparatus as in claim 3 wherein said adjustable pressure regulator is disposed in a first path from said coolant supply and where a second path is connected from said coolant supply in parallel to said first path; and where said apparatus includes further switchable valve means, having first and second input ports respectively connected to said first and second paths and an output port connected to said feed passageway of the cryosurgical instrument, said further switchable means being switchable to a first position during said freeze mode where said first path is connected to said feed passageway of the cryosurgical instrument and to a second position during said defrost mode where said second path is connected to said feed passageway whereby the freeze rate utilized in said freeze mode is adjustable depending upon the setting of said adjustable pressure regulator and where the temperature of said tissue contacting portion during the defrost mode is determined by said elevated pressure of the coolant at said coolant supply.

5. Apparatus as in claim 4 where two coolant supplies are respectively employed for freeze and defrost modes.

6. Apparatus as in claim 1 where said pressure maintaining means includes means for maintaining said vapor pressure substantially constant at approximately at least what it is at room temperature.

7. Apparatus as in claim 1 where said pressure maintaining means includes means for increasing the vapor pressure to an increased value greater than what it is at said room temperature and for maintaining the increased vapor pressure at approximately at least said increased value.

8. Apparatus as in claim 7 where said pressure maintaining means includes means for maintaining said vapor pressure substantially constant at approximately at said increased value.

9. Apparatus as in claim 7 where said pressure maintaining means includes a heat source for heating said coolant supply; and pressure sensing means for sensing the pressure of the output gas from said coolant supply to control said heat source and thereby maintain said increased vapor pressure.

10. Apparatus as in claim 9 where said pressure sensing means comprises a transducer responsive to the pressure of said output gas supplied by the cylinder to convert the sensed pressure to an electrical signal for regulating the electrical current flowing through said electrical resistance wiring and thus the heat supplied from the mantle to thereby effect the maintenance of the elevated vapor pressure at a substantially constant level.

11. Apparatus as in claim 7 where said pressure maintaining means includes means for heating the coolant to thereby at least replace the heat lost by evaporation of the coolant in the container as coolant is delivered to the cryosurgical instrument.

12. Apparatus as in claim 11 where said heating means is externally disposed with respect to said container.

13. Apparatus as in claim 1 where said pressure maintaining means includes means for heating the coolant to thereby at least replace the heat lost by evaporation of the coolant in the container as coolant is delivered to the cryosurgical instrument.

14. Apparatus as in claim 13 where said heating means is externally disposed with respect to said container.

15. Apparatus as in claim 13 where said coolant supply is a cylindrical container and said heating means includes a mantle disposed about said cylinder, said mantle including electrical resistance wiring for heating said cylinder.

16. Apparatus as in claim 15 where said cylinder is a size "E" cylinder.

17. Apparatus as in claim 1 where said cryosurgical instrument further has a hollow tissue contacting portion and a discharge path disposed outside of said feed passageway, both said feed passageway and said discharge path being disposed within said hollow tissue contacting portion so that the coolant discharged through said expansion means lowers the temperature of said tissue contacting portion to a necrosing temperature sufficient to effect necrosing of human tissue or the like.

18. Apparatus as in claim 17 where the freeze rate at which said temperature of the tissue contacting portion is lowered to said necrosing temperature is at least 15° C. per second when said coolant is maintained at the elevated pressure.

19. Apparatus as in claim 18, where said freeze rate is at least 20° C. per second.

20. Apparatus as in claim 1 where said pressure maintaining means includes means for adjusting the vapor pressure of the coolant to a desired value.

21. Apparatus as in claim 1 where said pressure maintaining means maintains said vapor pressure at approximately at least what it is at room temperature until it can no longer be so maintained because of emptying of coolant from the container.

22. Apparatus as in claim 1 where said room temperature is approximately 68° F.

23. Cryosurgical apparatus for necrosing human tissue or the like, said apparatus comprising
- a coolant supply where said coolant is disposed within a container as a liquid under its own vapor pressure;
- a cryosurgical instrument having a hollow tissue contacting portion and a coolant expansion means disposed at the distal end of a feed passageway and a discharge path disposed outside of said passageway, both said feed passageway and said discharge path being disposed within said hollow tissue contacting portion;
- means for supplying said coolant to the first passageway of said cryosurgical instrument so that the coolant expanded through said expansion means lowers the temperature of said tissue contacting portion to a necrosing temperature sufficient to effect said necrosing of said human tissue or the like; and
- means connected to said discharge path for exhausting said coolant from said apparatus;
- switchable valve means connected to said discharge path of said cryosurgical instrument, said switchable valve means being switchable to a first position to exhaust said coolant from said apparatus and to a second position for closing the switchable valve means;
- defrost discharge means also connected to said discharge path of said cryosurgical instrument, the flow impedance of said defrost discharge means being substantially greater than that of said switchable valve means when it is in its said first position and substantially less than that of the switchable valve means when it is in its said second position,
- whereby the coolant is supplied to said feed passageway of said cryosurgical instrument for both a freeze mode and a defrost mode of operation of said apparatus, said apparatus being in its freeze mode when said switchable valve means is in its first position so that said coolant discharges through said switchable valve means and said apparatus being in its defrost mode when it is in its second position so that said coolant discharges through said defrost discharge means and where the temperature of said tissue contacting portion in the defrost mode is greater than 0° C. as long as said apparatus is in the latter mode.

24. Apparatus as in claim 23 including an adjustable pressure regulator responsive to the output gas from said coolant supply for adjustably regulating the pressure of the coolant applied to said feed passageway of the cryosurgical instrument.

25. Apparatus as in claim 24 where said adjustable pressure regulator is disposed in a first path from said coolant supply and where a second path is connected from said coolant supply in parallel to said first path; and where said apparatus includes further switchable valve means, having first and second input ports respectively connected to said first and second paths and an output port connected to said feed passageway of the cryosurgical instrument, said further switchable means being switchable to a first position during said freeze mode where said first path is connected to said feed passageway of the cryosurgical instrument and to a second position during said defrost mode where said second path is connected to said feed passageway
- whereby the freeze rate utilized in said freeze mode is adjustable depending upon the setting of said adjustable pressure regulator and where the temperature of said tissue contacting portion during the defrost mode is determined by the pressure of the coolant at said coolant supply.

26. Cryosurgical method comprising the steps of
- providing a coolant supply container where a coolant selected from the groups consisting of nitrous oxide, carbon dioxide, Freon 13 or Freon 23 is disposed within a container in its liquid and gaseous phases, the critical temperature of said coolant being greater than the ambient temperature of the container;
- maintaining said vapor pressure at approximately at least what it is at said ambient temperature of the coolant supply;
- providing a cryosurgical instrument having a coolant expansion means disposed at the distal end of a feed passageway, and
- supplying said coolant to the feed passageway of said cryosurgical instrument so that the temperature of the coolant discharged through said expansion means is lowered,
- whereby said vapor pressure is maintained at approximately at least what it is at said ambient temperature during said supplying of the coolant to the feed passageway of the cryosurgical instrument.

27. A method as in claim 26 where said pressure elevating step includes
- heating said coolant supply so that said vapor pressure is greater than what it would be at said ambient temperature; and
- sensing the pressure of the output gas from said coolant supply to control said heat source and thereby maintain said elevated vapor pressure substantially constant.

28. A method as in claim 26 where said pressure maintaining step includes the step of maintaining said vapor pressure substantially constant at approximately at least what it is at said ambient temperature of the coolant supply.

29. A method as in claim 26 where said pressure maintaining step includes the steps of increasing the vapor pressure to an increased value greater than what it would be at said ambient temperature and for maintaining the vapor pressure at approximately at least said increased value.

30. A method as in claim 29 where said pressure maintaining step includes the step of maintaining said vapor pressure substantially at approximately said increased value.

31. A method as in claim 26 where said pressure maintaining step includes the step of heating the coolant to thereby at least replace the heat lost by evaporation of the coolant in the container as coolant is delivered to the cryosurgical instrument.

32. A method as in claim 31 where the heat for heating the coolant originates from a source externally disposed with respect to the container therefor.

33. A method as in claim 26 where said cryosurgical instrument further has a hollow tissue contacting portion and a discharge path disposed outside of said feed passageway, both said feed passageway and said discharge path being disposed within said hollow tissue contacting portion so that the coolant discharged through said expansion means lowers the temperature of said tissue contacting portion to a necrosing temperature sufficient to effect necrosing of human tissue or the like.

34. A method as in claim 33 where the freeze rate at which said temperature of the tissue contacting portion is lowered to said necrosing temperature is at least 15° C. per second when said coolant is maintained at the elevated pressure.

35. A method as in claim 34 where said freeze rate is at least 20° C. per second.

36. A method as in claim 26 where said ambient temperature is approximately 68° F.

37. A method as in claim 26 where said vapor pressure is maintained at approximately at least what it is at said ambient temperature until it can no longer be so maintained because of emptying of the coolant from the container.

38. Cryosurgical apparatus comprising
a coolant supply where a coolant selected from the groups consisting of nitrous oxide, carbon dioxide, Freon 13 or Freon 23 is disposed within a container as a liquid due to the pressure of its own vapor where the critical temperature of said coolant is greater than the ambient temperature of the container;
pressure maintaining means for maintaining said pressure of the vapor at approximately at least what it is at said ambient temperature of the container;
a cryosurgical instrument having a coolant expansion means disposed at the distal end of a feed passageway; and
means for supplying said coolant to the feed passageway of said cryosurgical instrument so that the temperature of the coolant discharged through said expansion means is lowered
whereby said pressure maintaining means maintains said vapor pressure at approximately at least what it is at said ambient temperature during said supplying of the coolant to the feed passageway of the cryosurgical instrument.

39. Apparatus as in claim 38 where said pressure maintaining means includes means for maintaining said vapor pressure substantially constant at at least what it is at said ambient temperature of the container.

40. Apparatus as in claim 38 where said pressure maintaining means includes means for increasing the vapor pressure to an increased value greater than what it is at said ambient temperature and for maintaining the increased vapor pressure at at least said increased value.

41. Apparatus as in claim 40 where said pressure maintaining means includes means for maintaining said vapor pressure substantially constant at approximately said increased value.

42. Apparatus as in claim 40 where said pressure maintaining means includes means for heating the coolant to thereby at least replace the heat lost by evaporation of the coolant in the container as coolant is delivered to the cryosurgical instrument.

43. Apparatus as in claim 42 where said heating means is externally disposed with respect to said container.

44. Apparatus as in claim 40 where said cryosurgical instrument further has a hollow tissue contacting portion and a discharge path disposed outside of said feed passageway, both said feed passageway and said discharge path being disposed within said hollow tissue contacting portion so that the coolant discharged through said expansion means lowers the temperature of said tissue contacting portion to a necrosing temperature sufficient to effect necrosing of human tissue or the like.

45. Apparatus as in claim 44 where the freeze rate at which said temperature of the tissue contacting portion is lowered to said necrosing temperature is at least 15° C. per second when said coolant is maintained at the elevated pressure.

46. Apparatus as in claim 40 where said pressure maintaining means maintains said vapor pressure at approximately at least what it is at said ambient temperature until it can no longer be so maintained because of emptying of the coolant from the container.

47. Apparatus as in claim 40 where said ambient temperature is approximately 68° F.

48. Apparatus as in claim 38 where said pressure maintaining means includes means for heating the coolant to thereby at least replace the heat lost by evaporation of the coolant in the container as coolant is delivered to the cryosurgical instrument.

49. Apparatus as in claim 48 where said heating means is externally disposed with respect to said container.

50. Cyrosurgical apparatus comprising
a coolant supply where a coolant selected from the groups consisting of nitrous oxide, carbon dioxide, Freon 13 or Freon 23 is disposed within a container as a liquid due to the pressure of its own vapor, said pressure being at a first value;
a cryosurgical instrument having a coolant expansion means disposed at the distal end of a feed passageway;
a supply line for supplying said coolant from said supply container to the feed passageway of said cryosurgical instrument so that the temperature of the coolant discharged through said expansion means is lowered; and
pressure maintaining means including means externally disposed with respect to said container for heating the coolant for maintaining the vapor pressure of the coolant in the supply container at approximately at least said first value to thereby at least replace the heat lost by evaporation of the coolant in the container as coolant is delivered to the cryosurgical instrument.

51. Apparatus as in claim 50 where said pressure maintaining means includes means for maintaining said vapor pressure substantially constant at approximately at least said first value.

52. Apparatus as in claim 50 where said heating means includes means for increasing the vapor pressure to an increased value greater than said first value and for maintaining the increased vapor pressure at approximately at least said increased value.

53. Apparatus as in claim 52 where said pressure maintaining means includes means for maintaining said vapor pressure substantially constant at approximately said increased value.

54. Apparatus as in claim 52 where said cryosurgical instrument further has a hollow tissue contacting portion and a discharge path disposed outside of said feed passageway, both said feed passageway and said discharge path being disposed within said hollow tissue contacting portion so that the coolant discharged through said expansion means lowers the temperature of said tissue contacting portion to a necrosing temperature sufficient to effect necrosing of human tissue or the like.

55. Apparatus as in claim 54 where the freeze rate at which said temperature of the tissue contacting portion is lowered to said necrosing temperature is at least 15° C. per second when said coolant is maintained at the elevated pressure.

56. Apparatus as in claim 52 where said pressure maintaining means includes means for adjusting the vapor pressure of the coolant to a desired value.

* * * * *